United States Patent [19]

Trobisch et al.

[11] 3,983,004

[45] Sept. 28, 1976

[54] PREPARATION OF A DIAGNOSTIC AGENT FOR MEASURING THE COAGULABILITY OF BLOOD

[75] Inventors: Heiner Trobisch, Marburg an der Lahn; Horst Schwinn, Marbach-Michelbach, both of Germany

[73] Assignee: Behringwerke Aktiengesellschaft, Marburg an der Lahn, Germany

[22] Filed: Nov. 11, 1974

[21] Appl. No.: 522,759

[30] Foreign Application Priority Data

Nov. 13, 1973 Germany............................ 2356493

[52] U.S. Cl.............................. 195/99; 23/230 B; 195/103.5 R; 424/2; 424/105
[51] Int. Cl.².................. G01N 31/00; G01N 33/16; A61K 35/48
[58] Field of Search...................... 195/103.5 R, 99; 23/230 B; 424/101, 105, 2

[56] References Cited
UNITED STATES PATENTS

| | | |
|---|---|---|
| 2,687,980 | 8/1954 | Blanchard et al............ 195/103.5 R |
| 2,847,347 | 8/1958 | Singher et al................ 195/103.5 R |
| 3,522,148 | 7/1970 | Adam et al.................. 195/103.5 R |
| 3,862,314 | 1/1975 | Zwisler et al...................... 424/105 |

*Primary Examiner*—David M. Naff
*Assistant Examiner*—C. A. Fan
*Attorney, Agent, or Firm*—Curtis, Morris & Safford

[57] ABSTRACT

A diagnostic agent containing thromboplastin sensitive to factor VII and factor X for measuring the coagulability of blood is prepared by extracting an aqueous suspension of thrombogenic tissue at pH 10 to 12, acidifying the extract, separating the extract from the tissue and adding a water-soluble calcium salt to the extract. The agent can be stabilized by adding to the extract cholanic acid and a water-soluble heavy metal-II-salt.

15 Claims, No Drawings

PREPARATION OF A DIAGNOSTIC AGENT FOR MEASURING THE COAGULABILITY OF BLOOD

The present invention relates to a diagnostic agent for the measurement of blood coagulability, a process for its manufacture and a stabilizer for this agent.

Especially, it relates to a diagnostic agent consisting of calcium ions and of thromboplastin that is obtained from the thrombogenic tissue of human or animal origin, especially from human placenta tissue.

The invention also relates to the manufacture of a standardized factor VII sensitive and factor X-sensitive thromboplastin consisting of thrombogenic tissue.

Further object of the invention is a stabilizer for a thromboplastin containing calcium ions.

A test to determine disturbances in the exogenic coagulation system was first published in 1937 as the single-phase coagulation test according to Quick. The function of the exogenic coagulation system, which is based on the interaction of the coagulation factors VII, X, V, II and I, is determined by adding a standardized tissue extract from the organs of warm-blooded animals, which extract is denominated as thromboplastin. Under the action of the thromboplastin, the coagulation factor VII (Proconvertin) is activated and in turn converts the factor X (Stuart-Prower-F.) into its active form. In the presence of calcium ions, an active enzyme-lipid complex is formed from phospholipides and the activated coagulation factors X and V (Accelerin), and this complex converts the factor II (Prothrombin) into its active form, thrombin. The factor I (Fibrinogen) of the plasma is converted into fibrin in proportion to the speed at which thrombin is formed. The coagulation time measured for a control plasma in seconds is taken as a measure for judging coagulation capability.

The so-called Quick value permits the detection of inborn or acquired insufficiencies of the factors which are part of the exogenic coagulation system. Furthermore, the measurement of the single-phase coagulation time allows the control of oral anti-coagulant therapy. The thromboplastin used for this purpose has, on the one hand, the considerable quality criterion of being free from the coagulation factors of the exogenic system, especially from thrombin, but, on the other hand, of being highly sensitive towards these factors.

Processes for the manufacture of highly active thromboplastin have been described in the literature many times. In some cases, human placentae are used for this purpose as a starting substance. However, it has not been proposed until now how to obtain factor VII sensitive and factor X-sensitive thromboplastins from thrombogenic tissue, especially from placentae.

In the known processes for obtaining of thromboplastin from fresh washed placental tissues, an aqueous extraction is generally used. In other processes for obtaining thromboplastin tissue homogenizates are extracted with aqueous ethanol or phenol. In all these processes, the pH values are maintained in the range of neutral to slightly alkaline. Thromboplastin preparations that have been obtained according to these processes can be stored and used only to a limited extent in spite of various stabilizing measures, such as treatment with ultraviolet light or storage with the exclusion of air. They are not entirely free from thrombin and are, especially, not sensitive enough towards the factors VII and X to allow exact differentiations between normal and pathological coagulation pictures.

Now it has been found that the above-described drawbacks of described above of thromboplastin preparations do not arise using a diagnostic agent for the measurement of blood coagulability that contains thromboplastin and calcium ions and that is characterized by a content of factor VII sensitive and factor X-sensitive thromboplastin free from thrombin. The agent is extracted from an aqueous suspension of thrombogenic tissue, washed until free from blood, at pH 10 to 12 for a period of 15 minutes to 48 hours at 30°C to 1°C, whereby the shortest extraction time is to be correlated with the highest temperature, the longest extraction time with the lowest temperature, and the values between those peaks are to be correlated analogously. The extract is then separated from the tissue after a treatment in the slightly acid pH range.

An especially sensitive thromboplastin is obtained when the extraction is effected at a pH between 11.4 and 11.8, preferably at 30°C for 15 minutes, at 22°C for 30 minutes, or at 4°C for 20 hours, and the tissue is after-treated before separating the extraction solution at pH values of from 4.5 to 7.0, preferably 6.0 to 6.4.

To the thromboplastin obtained in this manner, calcium ions are added in the form of a waste-soluble Ca-salt, preferably calcium chloride.

It has also been found that excellent stability upon storage is imparted to the diagnostic by adding a cholanic acid, preferably desoxycholic acid or cholic acid, and a water-soluble heavy metal salt, such as $UO_2^{++}$-, $Zn^{++}$-, $Ni^{++}$-salts, especially a manganese-II salt, preferably manganese-II-chloride.

An especially good stability, that also enables the diagnostic reagent to be lyophilized, is obtained by the addition of a sugar alcohol, for example mannitol or sorbitol or a mono- or disaccharide.

The optimal weight ratio is mannitol: desoxycholic acid: manganese-II-chloride = 300 : 3 : 1, the manganese-II-chloride being in $10^{-3}$ to $10^{-4}$ molar solution, preferably $5 \times 10^{-4}$ molar solution.

Such a diagnostic agent capable of being readily resuspended in distilled water is fully active during storage as a solution at 37°C up to 10 hours and durable for at least 2 days at 20°C. In the lyophilized form, the agent does not show any decrease of activity during storage in a refrigerator (at about 4°C) for 2 years.

The most active factor VII-sensitive thromboplastins can be obtained from the human brain. More readily accessible are human placentae that also contain thromboplastins of high activity. In order of decreasing thromboplastins activity, there may be mentioned the brains of monkey and rabbit, the lung of rabbits, and the brains of cattle and swine.

The present invention permits obtaining a diagnostic agent that can be used, for example, for the determination of the single-phase coagulation time according to Quick using the following method: 0.1 ml of citrated or oxalated plasma to be tested for its physiological coagulability is pipetted into a test tube preheated to 37°C. After an incubation period of 30 seconds, 0.2 ml of a preheated aqueous suspension of calcium thromboplastin obtained from human placentae according to the invention is added and from that moment the time is measured until coagulation takes place. The coagulation time so obtained of the test plasma is correlated to a coagulation time of a mixed plasma of at least 5 sound donors. For this purpose, the mixed plasma is incubated with the calcium thromboplastin of the invention in an undiluted state, and in a dilution of 1 : 2, 1 : 4 and 1 : 10 in the same manner as described with regard to the test plasma. The resulting coagulation times are coordinated as abscissa to the reciprocal values of the dilutions as ordinate, yielding a linear steep standard curve. Beginning at the coagulation time of the test plasma on the abscissa, the point of intersection is determined on the standard curve and the corresponding reciprocal value is read off on the ordinate. The following calculation yields the value in percentage of the coagulation time of the test plasma with respect to a normal mixed plasma:

1: value of the ordinate section × 100 = value in % of the coagulation activity as value in % of the standard.

For example, when the plasma dilutions of a normal mixed plasma indicated in the following Table are coordinated with the resulting coagulation times, it is possible to draw the standard curve.

| Plasma dilution | concentrated | 1:2 | 1:4 | 1:10 |
|---|---|---|---|---|
| Coagulation times in seconds | 11.5 | 17.0 | 30.4 | 81.3 |

A typical factor VII insufficient plasma leads to a coagulation time of about 58 seconds, which is about 12 % of the standard as per the standard curve.

A measure of the sensivity of the thromboplastin is given by the quotient of the coagulation time of a pathological plasma and a standardized mixed plasma — the so-called prothrombin ratio. The higher this quotient, the greater the capability of the thrombo-plastin to detect a coagulation insufficiency. In the present case, the prothrombin ratio is about 5. This ratio demonstrates that the diagnostic agent according to the invention is extraordinarily suitable for the detection of pathological coagulation states, especially of factor VII insufficiencies.

When the diagnostic agents are obtained from rabbit brains, rabbit lungs or swine placentae according to the invention, a normal mixed plasma shows, for the determination of the single-phase coagulation time according to Quick, the values as summarized in the following Table:

|  | concentrated | 1:2 | 1:4 | 1:10 |
|---|---|---|---|---|
| rabbit brain | 16.5 | 24.8 | 43.1 | 111.2 |
| rabbit lung | 10.2 | 14.2 | 22.4 | 52.5 |
| swine placentae | 27.1 | 41.4 | 66.5 | 210.0 |

The following Examples serve to illustrate the invention:

EXAMPLE 1:

15 kg of lyophilized human placentae were comminuted by means of a meat mincer. The placental homogenizate was washed 18 times with 120 l portions of a 0.9 % sodium chloride solution at +10°C and in each washing operation the water was eliminated by sedimentation and decantation. The last supernatant was then colorless. The placental homogenizate washed in this manner was centrifuged at 3,000 g to get rid of the residual washing water. The moist sediment was dried for 30 hours in a closed freeze-drying device until a residual moisture of 5 % was reached. The yield of dry material was about 1.5 kg.

1.5 kg of the dried placental tissue washed until free from blood were suspended with 30 l of distilled water and comminuted for 10 minutes at 10°C by means of a homogenizer (Ultra Turrax of Messrs. Janke and Kunkel, type 100/2 M). Thereafter, 5 N sodium hydroxide solution was added, while stirring thoroughly, in such an amount (about 210 ml) as to reach pH 11.5. The mixture was stirred for 25 minutes and then its pH was adjusted to 6.6 by adding 5 N hydrochloric acid (about 210 ml). The mixture was treated a second time with the homogenizer for a period of 30 minutes. The residual tissue was centrifuged at 3,000 g, whereupon 20 l of thromboplastin were obtained.

To 1 liter each of thromboplastin, 1.1 g of calcium chloride, 30 g of mannitol, 0.3 G of Desoxycholic acid and 0.1 g of manganese-II-chloride-tetrahydrate were added. The pH was exactly adjusted to 6.3 by adding a slight amount of hydrochloric acid or sodium hydroxide solution. The thromboplastin solution was filled into glass bottles in amounts of 2.0 ml each and lyophilized. In its lyophilized state the thromboplastin did not suffer any loss of activity.

EXAMPLE 2:

The grey substance of rabbit brain was obtained in known manner and washed with a 0.9 % NaCl-solution until free from blood. The washing operation was controlled by spectrophotometric determination of the residual hemoglobin.

120 g of the still moist brain tissue were infused with 400 ml of distilled water and comminuted for 10 minutes at 10°C by means of a laboratory homogenizer (by Messrs. Janke & Kunkel). The pH was adjusted to 11.6 with 5 N NaOH while stirring thoroughly and the mixture was maintained in that state for 25 minutes.

Then, the pH was adjusted to 6.4 with 5 N HCl and the mixture was homogenized once more, for 30 minutes, by means of the homogenizer described above, while cooling slightly. The tissue was centrifuged at 3,000 g and the thromboplastin-containing supernatant (280 ml) was obtained by decanting.

To 100 ml each of thromboplastin, 0.1 g of calcium chloride, 3.0 g of sorbitol, 30 mg of desoxycholic acid, and 14 mg of zinc sulfate (7 $H_2O$) were added.

The pH value of the thromboplastin was adjusted to exactly 6.3 and the thromboplastin was filled into containers in amounts of 2 ml each and lyophilized.

EXAMPLE 3:

240 g of moist swine placentae washed until free from blood were infused with 400 ml of distilled water and comminuted for 10 minutes at 10°C by means of a laboratory homogenizer (by Messrs Janke & Kunkel). Thereafter, the pH was adjusted to 11.6 with 5 N NaOH, while stirring thoroughly and the mixture was maintained in that state for 25 minutes.

Thereafter the pH was adjusted to 6.4 with 5 N HCl and the mixture was homogenized once more, for 30 minutes, by means of the above homogenizer while cooling slightly. Then, the tissue was centrifuged at 3,000 g and the thromboplastin-containing supernatant (250 ml) was obtained by decanting.

To 100 ml each of the thromboplastin, 0.1 g of calcium chloride, 3.0 g of mannitol, 0.3 g of desoxycholic acid and 0.1 g of manganese-II-chloride × 4 H₂O are added.

The pH value of the thromboplastin was adjusted to exactly 6.3 and the solution was filled into containers in amounts of 2 ml each and lyophilized.

What is claimed is:

1. A method for making a diagnostic agent for measuring the coagulability of blood, which method comprises washing a thrombogenic tissue until it is free from blood, preparing an aqueous suspension of the washed tissue containing sufficient lye to provide the suspension with a pH of from 10 to 12, extracting the tissue in the suspension at said pH for 15 minutes to 48 hours at a temperature from 30°C. to 1°C., whereby the shortest extraction time is correlated with the highest temperature, the longest extraction time with the lowest temperature, and values between these are correlated analogously, acidifying the aqueous suspension to impart a slightly acid pH, separating the extract from the tissue, and adding a water-soluble calcium salt to the extract.

2. A method as in claim 1 wherein said aqueous suspension of washed tissue is extracted at a pH between 11.4 and 11.8.

3. A method as in claim 2 wherein the extraction is performed for 15 minutes at 30°C.

4. A method as in claim 2 wherein the extraction is performed for 30 minutes at 22°C.

5. A method as in claim 2 wherein the extraction is performed for at least 20 hours at 4°C.

6. A method as in claim 1 wherein said aqueous suspension is acidified, after extraction, to a pH between 4.5 and 7.

7. A method as in claim 1 wherein said aqueous suspension is acidified, after extraction, to a pH between 6 and 6.4.

8. A method as in claim 1 wherein said thrombogenic tissue is human or animal brain tissue or placental tissue.

9. A method as in claim 1 which additionally comprises adding a cholanic acid and a water-soluble heavy metal-II-salt to the separated extract as stabilizers therefor.

10. A method as in claim 9 wherein said cholanic acid is desoxycholic acid and said heavy metal-II-salt is manganese-II-chloride.

11. A method as in claim 1 which additionally comprises adding a sugar alcohol, ammonosaccharide, or a disaccharide to the separated extract.

12. A method as in claim 11 wherein said sugar alcohol is mannitol.

13. A method as in claim 1 which additionally comprises adding mannitol, desoxycholic acid, and manganese-II-chloride to the separated extract in a weight ratio of 300:3:1.

14. A method as in claim 13 wherein manganese-II-chloride is present in said extract in a molar concentration from $10^{-3}$ to $10^{-4}$.

15. A diagnostic agent prepared by the method of claim 1.

* * * * *